(12) United States Patent
Szewczyk et al.

(10) Patent No.: US 10,561,590 B2
(45) Date of Patent: *Feb. 18, 2020

(54) DENTIFRICE COMPROMISING ZINC-AMINO ACID COMPLEX AND PHOSPHATES

(71) Applicant: Colgate-Palmolive Company, New York, NY (US)

(72) Inventors: Gregory Szewczyk, Flemington, NJ (US); Lisa Manus, Lawrenceville, NJ (US); Lyndsay Schaeffer-Korbylo, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/142,738

(22) Filed: Sep. 26, 2018

(65) Prior Publication Data

US 2019/0091117 A1 Mar. 28, 2019

Related U.S. Application Data

(63) Continuation of application No. 15/319,757, filed as application No. PCT/US2014/043051 on Jun. 18, 2014, now Pat. No. 10,130,571.

(51) Int. Cl.

| | | |
|---|---|---|
| *A61K 8/24* | (2006.01) | |
| *A61K 8/21* | (2006.01) | |
| *A61K 8/27* | (2006.01) | |
| *A61K 8/44* | (2006.01) | |
| *A61K 8/46* | (2006.01) | |
| *A61Q 11/00* | (2006.01) | |
| *A61K 8/25* | (2006.01) | |

(52) U.S. Cl.
CPC ............... *A61K 8/24* (2013.01); *A61K 8/21* (2013.01); *A61K 8/25* (2013.01); *A61K 8/27* (2013.01); *A61K 8/44* (2013.01); *A61K 8/442* (2013.01); *A61K 8/463* (2013.01); *A61Q 11/00* (2013.01); *A61K 2800/70* (2013.01)

(58) Field of Classification Search
None
See application file for complete search history.

(56) References Cited

U.S. PATENT DOCUMENTS

| | | | |
|---|---|---|---|
| 9,498,421 B2 | 11/2016 | Liu et al. | |
| 9,504,858 B2 | 11/2016 | Yuan et al. | |
| 9,763,865 B2 * | 9/2017 | Pan | A61K 8/27 |
| 9,775,792 B2 * | 10/2017 | Liu | A61K 8/27 |
| 9,901,523 B2 * | 2/2018 | Xu | A61K 8/27 |
| 9,913,784 B2 * | 3/2018 | Szewczyk | A61K 8/27 |
| 9,993,407 B2 * | 6/2018 | Liu | A61K 8/27 |
| 10,105,303 B2 * | 10/2018 | Pan | A61K 8/27 |
| 10,130,571 B2 * | 11/2018 | Szewczyk | A61K 8/24 |
| 2003/0165442 A1 * | 9/2003 | Baig | A23G 4/06 424/57 |
| 2014/0170086 A1 | 6/2014 | Pan et al. | |
| 2015/0313821 A1 | 11/2015 | Yuan et al. | |
| 2015/0313822 A1 | 11/2015 | Pan et al. | |
| 2015/0313827 A1 | 11/2015 | Hardy et al. | |
| 2015/0328095 A1 | 11/2015 | Pan et al. | |
| 2015/0328110 A1 | 11/2015 | Pan et al. | |
| 2015/0328111 A1 | 11/2015 | Liu et al. | |
| 2015/0328112 A1 | 11/2015 | Xu et al. | |
| 2015/0328117 A1 | 11/2015 | Pan et al. | |
| 2015/0328118 A1 | 11/2015 | Pan et al. | |
| 2015/0335552 A1 | 11/2015 | Liu et al. | |
| 2015/0335553 A1 | 11/2015 | Pan et al. | |
| 2015/0335554 A1 | 11/2015 | Pan et al. | |
| 2015/0342851 A1 | 12/2015 | Liu et al. | |

FOREIGN PATENT DOCUMENTS

| | | | |
|---|---|---|---|
| WO | WO 1986/000004 | 1/1986 | |
| WO | WO 1999/017735 | 4/1999 | |
| WO | WO 2004/054531 | 7/2004 | |
| WO | 2008/006725 | 1/2008 | |
| WO | 2009/060385 | 5/2009 | |
| WO | WO 2011/053291 | 5/2011 | |
| WO | WO 2012015420 A1 | 2/2012 | ........... A46B 11/001 |
| WO | WO-2014098818 A1 * | 6/2014 | ............... A61K 8/27 |
| WO | WO 2014098818 A1 | 6/2014 | ............... A61K 8/27 |
| WO | WO 2015/195118 | 12/2015 | |
| WO | WO 2015/195124 | 12/2015 | |

OTHER PUBLICATIONS

O.T.Quimby and H.W. McCune. Precipitation of Zinc Phosphates from Solutions of Sodium Ortho-, Pyro-, and Triphosphate. Analytical Chemistry, 29(2), 248-253. (Year: 1957).

International Search Report and Written Opinion of the International Searching Authority in PCT/US2014/043051, dated Feb. 18, 2015.

Wachi et al., 1982, "Antibacterial composition zinc oxide—solubilised by amino acid, amino acid hydrochloride and/or amino acid alkali metal salt," WPI Thomson AN: 1982-96021E; JP 1981004430.

* cited by examiner

*Primary Examiner* — Michael P Cohen

(57) ABSTRACT

Disclosed herein are dentifrices comprising a zinc amino acid complex together with soluble phosphate salts. Methods of making and using the dentifrices are also provided.

13 Claims, No Drawings

DENTIFRICE COMPROMISING ZINC-AMINO ACID COMPLEX AND PHOSPHATES

BACKGROUND

Dental erosion involves demineralization and damage to the tooth structure due to acid attack from nonbacterial sources. Erosion is found initially in the enamel and, if unchecked, may proceed to the underlying dentin. Dental erosion may be caused or exacerbated by acidic foods and drinks, exposure to chlorinated swimming pool water, and regurgitation of gastric acids. The tooth enamel is a negatively charged surface, which naturally tends to attract positively charged ions such as hydrogen and calcium ions, while resisting negatively charged ions such as fluoride ions. Depending upon relative pH of surrounding saliva, the tooth enamel will lose or gain positively charged ions such as calcium ions. Generally saliva has a pH between 7.2 to 7.4. When the pH is lowered and concentration of hydrogen ions becomes relatively high, the hydrogen ions will replace the calcium ions in the enamel, forming hydrogen phosphate (phosphoric acid), which damages the enamel and creates a porous, sponge-like roughened surface. If saliva remains acidic over an extended period, then remineralization may not occur, and the tooth will continue to lose minerals, causing the tooth to weaken and ultimately to lose structure.

Dentinal hypersensitivity is acute, localized tooth pain in response to physical stimulation of the dentine surface as by thermal (hot or cold) osmotic, tactile combination of thermal, osmotic and tactile stimulation of the exposed dentin. Exposure of the dentine, which is generally due to recession of the gums, or loss of enamel, frequently leads to hypersensitivity. Dentinal tubules open to the surface have a high correlation with dentine hypersensitivity. Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients.

Heavy metal ions, such as zinc, are resistant to acid attack. Zinc ranks above hydrogen in the electrochemical series, so that metallic zinc in an acidic solution will react to liberate hydrogen gas as the zinc passes into solution to form di-cations, $Zn^{2+}$. Zinc has been shown to have antibacterial properties in plaque and caries studies.

Soluble zinc salts, such as zinc citrate, have been used in dentifrice compositions, see, e.g., U.S. Pat. No. 6,121,315, but have several disadvantages. Zinc ions in solution impart an unpleasant, astringent mouthfeel, so formulations that provide effective levels of zinc, and also have acceptable organoleptic properties, have been difficult to achieve. Finally, the zinc ions will react with anionic surfactants such as sodium lauryl sulfate, thus interfering with foaming and cleaning. Zinc oxide and insoluble zinc salts, on the other hand, may do a poor job of delivering zinc to the teeth because of their insolubility.

A novel zinc-lysine complex ("ZLC") having the chemical structure $[Zn(C_6H_{14}N_2O_2)_2Cl]^+Cl^-$, has recently been described. See, e.g. PCT/US2012/70489 and PCT/US2012/70498, each filed on 19 Dec. 2012, and each incorporated by reference in its entirety. ZLC has the unusual property that under conditions of increasing dilution rather than going into or remaining in solution as the solution becomes more dilute, as would typically be the case for an ionic complex, the ZLC hydrolyzes, to provide a relatively insoluble zinc oxide precipitate.

In addition to providing tartar control in the product, phosphates have the ability to chelate zinc in aqueous solution. More often than not, the interaction between such phosphates and zinc is strong, however, decreasing the bioavailability and stability of organozinc coordination complexes.

While the prior art discloses the use of various oral compositions for the treatment of dentinal hypersensitivity, dental caries, and enamel erosion and demineralization, there is still a need for additional compositions and methods that provide improved performance in such treatments.

SUMMARY

We have discovered that when phosphates are added to dentifrice formulations comprising zinc-amino acid complexes under low water conditions, rather than disrupting the complexes by chelating the zinc, the phosphates surprisingly preserves the complex. This results in increased antibacterial efficacy, because the intact complex can be taken up by bacteria, thereby killing the bacteria and disrupting biofilm growth, the amino acid (which could otherwise encourage bacterial growth) is not released. The formulations also have better formulation aesthetics, as the zinc is not free to impart an astringent taste to the formulation and it does not interfere with the foaming properties of antionic surfactants such as sodium lauryl sulfate. Phosphates thus have an important role in controlling the bioavailability, delivery, and stability of the zinc-amino acid complex active.

The zinc-amino acid complex forms a soluble cationic moiety, which in turn may form a salt with a halide or other anion. When placed in formulation, this complex provides an effective concentration of zinc ions to the enamel, thereby protecting against erosion, reducing bacterial colonization and biofilm development, and providing enhanced shine to the teeth. Moreover, upon use, the formulation provides a precipitate that can plug the dentinal tubules, thereby reducing the sensitivity of the teeth. While providing efficient delivery of zinc in comparison to formulations with insoluble zinc salts, the formulations comprising the zinc-amino acid complex do not exhibit the poor taste and mouthfeel, poor fluoride delivery, and poor foaming and cleaning associated with conventional zinc-based oral care products using soluble zinc salts.

The novel complex designated ZLC, may be formed, for example, from a mixture of zinc oxide and lysine hydrochloride. ZLC has the chemical structure $[Zn(C_6H_{14}N_2O_2)_2Cl]^+Cl^-$, and may exist in solution of the cationic cation $([Zn(C_6H_{14}N_2O_2)_2Cl]^+)$ and the chloride anion, or may be a solid salt, e.g., a crystal, optionally in mono- or dihydrate form.

We have also surprisingly discovered that the ZLC itself is taken up by bacteria, so that the antibacterial activity is not due merely to release of zinc ions. Upon use, some portion of the ZLC may degrade due to dilution and release zinc ions, forming a ZnO precipitate, which can deposit on the enamel and help plug the microtubules associated with erosion and hypersensitivity. But the ZLC can also be taken up directly by the bacteria, without degradation of the complex, providing additional antibacterial activity.

Phosphate salts in dentifrice formulations comprising zinc-amino acid complexes, for example ZLC, unexpectedly promote stability of the complex between the zinc and the amino acid. Within the typical dentifrice formulation, the interaction between zinc and amino acid can be perturbed by other formulation components, such as sodium lauryl sulfate (SLS) often used in toothpaste formulation to provide foam. The presence of phosphate seems to prevent this interference with the complex.

The disclosure thus provides a dentifrice composition, for example an oral gel or toothpaste, that comprises
(i) a zinc-amino acid complex, e.g, a zinc-lysine-chloride complex, e.g., ZLC;
(ii) one or more soluble phosphate salts, e.g. comprising tetrasodium pyrophosphate (TSPP), sodium tripolyphosphate (STPP), tetrapotassium pyrophosphate (TKPP), or combinations thereof; and
(iii) a dentifrice base,
wherein the composition comprises water in the amount of 1-20%, e.g., 5-18%, e.g. 7-19%, e.g. 8-17%, e.g. 9-16%, e.g. 10-15%, e.g. about 10% by weight.

The compositions may optionally further comprise one or more of a fluoride source, one or more abrasives, surfactants, foaming agents, vitamins, polymers, enzymes, humectants, thickeners, antimicrobial agents, preservatives, flavorings, and/or colorants.

The disclosure further provides methods of using the compositions of the disclosure to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying a composition of the disclosure to the teeth.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

DETAILED DESCRIPTION

The following description of the preferred embodiment(s) is merely exemplary in nature and is in no way intended to limit the disclosure, its application, or uses.

The disclosure therefore provides, in a first embodiment, a dentifrice (Composition 1), for example an oral gel or toothpaste, that comprises
(i) a zinc-amino acid complex, e.g, a zinc-lysine-chloride complex, e.g., ZLC;
(ii) one or more soluble phosphate salts, e.g. selected from tetrasodium pyrophosphate (TSPP), sodium tripolyphosphate (STPP), tetrapotassium pyrophosphate (TKPP), and combinations thereof; and
(iii) a dentifrice base,
wherein the dentifrice comprises water in the amount of 1-15%, e.g., 8-12%, e.g. about 10% by weight.

The dentifrice base may comprise, e.g., one or more of a fluoride source, abrasives, surfactants, foaming agents, vitamins, polymers, enzymes, humectants, thickeners, antimicrobial agents, preservatives, flavorings, and/or colorants.

The disclosure thus includes, e.g., 1.1. Composition 1 wherein the amino acid is selected from lysine, glycine and arginine, in free or orally acceptable acid addition salt form, e.g., hydrochloride form.
1.2. Composition 1 or 1.1 wherein the amino acid is a basic amino acid, e.g., arginine or lysine, in free or orally acceptable salt form.
1.3. Any of the foregoing compositions further comprising a halide in ionic association with the zinc and amino acid.
1.4. Any of the foregoing compositions wherein the molar ratio of Zn:amino acid is from 3:1 to 1:5, e.g., about 1:2 and the molar ratio of Zn:halide where present is from 3:1 to 1:3, e.g., about 1:2.
1.5. Any of the foregoing compositions wherein the zinc-amino acid complex is formed, in whole or in part, in situ after the composition is applied.
1.6. Any of the foregoing compositions wherein the zinc-amino acid complex is formed, in whole or in part, in situ after the composition is formulated.
1.7. Any of the foregoing compositions, wherein the amino acid is lysine.
1.8. Any of the foregoing compositions, wherein zinc is present in an amount of 0.05 to 10% by weight of the composition, optionally at least 0.1, at least 0.2, at least 0.3, at least 0.4, at least 0.5, at least 1, at least 2, at least 3, or at least 4 up to 10% by weight of the composition, e.g. about 1-3%, e.g., about 2-2.7% by weight.
1.9. Any of the foregoing compositions, wherein amino acid is present in an amount of 0.05 to 30% by weight of the composition, optionally at least 0.1, at least 0.2, at least 0.3, at least 0.4, at least 0.5, at least 1, at least 2, at least 3, at least 4, at least 5, at least 10, at least 15, at least 20 up to 30% by weight, e.g., about 1-10% by weight.
1.10. Any of the foregoing compositions, wherein a molar ratio of zinc to amino acid is 2:1 to 1:4, optionally 1:1 to 1:4, 1:2 to 1:4, 1:3 to 1:4, 2:1 to 1:3, 2:1 to 1:2, or 2:1 to 1:1, e.g., about 1:2 or 1:3
1.11. Any of the foregoing compositions comprising a halide in ionic association with the zinc and amino acid, wherein the halide is selected from the group consisting of fluorine, chlorine, and mixtures thereof
1.12. Any of the foregoing compositions wherein the zinc amino acid complex is a zinc lysine chloride complex (e.g., $(ZnLys_2Cl)^+Cl^-$ or $(ZnLys_3)^{2+}Cl_2$) or a zinc arginine chloride complex.
1.13. Any of the foregoing compositions, wherein the zinc amino acid complex is a zinc lysine chloride complex, e.g., ZLC, e.g., a zinc lysine chloride complex having the chemical structure $[Zn(C_6H_{14}N_2O_2)_2Cl]^+Cl^-$, either in solution of the cationic complex (e.g., $[Zn(C_6H_{14}N_2O_2)_2Cl]^+$) and the chloride anion, or in solid salt form, e.g., crystal form, optionally in mono- or dihydrate form.
1.14. Any of the foregoing compositions in the form of a clear gel which provides a zinc oxide precipitate when diluted.
1.15. Any of the foregoing compositions in the form of a dentifrice, e.g., wherein the zinc-amino acid complex is present in an effective amount, e.g., in an amount of 0.5-4% by weight of zinc, e.g., about 1-3% by weight of zinc, in a dentifrice base.
1.16. Any of the foregoing compositions in the form of a dentifrice, wherein the dentifrice base comprises an abrasive, e.g., an effective amount of a silica, e.g., 10-30%, e.g., about 20%.
1.17. Any of the foregoing compositions wherein the zinc-amino acid complex is present in an effective amount, e.g., in an amount of 0.1-3% by weight of zinc, e.g., about 0.2-1% by weight of zinc.
1.18. Any of the foregoing compositions wherein the zinc-amino acid complex is ZLC.

1.19. Any of the foregoing compositions wherein the zinc-amino acid complex is ZLC and is present in an amount of 2-6% of the composition by weight.
1.20. Any of the foregoing compositions wherein by "soluble phosphate salts" is meant an orally acceptable phosphate salt having a solubility in water of at least 1 g/100 ml at 25° C.
1.21. Any of the foregoing compositions wherein the one or more soluble phosphate salts are sodium and/or potassium salts of pyrophosphates and/or polyphosphates, e.g., tripolyphosphates.
1.22. Any of the foregoing compositions wherein the one or more soluble phosphate salts comprise tetrasodium pyrophosphate (TSPP), sodium tripolyphosphate (STPP), tetrapotassium pyrophosphate (TKPP), or combinations thereof.
1.23. Any of the foregoing compositions wherein the one or more soluble phosphate salts are present in an amount of 1-20%, e.g., 2-8%, e.g., ca. 5%, by weight of the composition.
1.24. Any of the foregoing compositions further comprising an effective amount of a fluoride ion source, e.g., providing 500 to 3000 ppm fluoride.
1.25. Any of the foregoing compositions wherein the dentifrice base comprises an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.
1.26. Any of the foregoing compositions wherein the dentifrice base comprises a humectant, e.g., selected from glycerin, sorbitol, propylene glycol, polyethylene glycol, xylitol, and mixtures thereof, e.g. comprising at least 30%, e.g., 40-50% glycerin, by weight of the composition.
1.27. Any of the preceding compositions wherein the dentifrice base comprises one or more surfactants, e.g., selected from anionic, cationic, zwitterionic, and nonionic surfactants, and mixtures thereof.
1.28. Any of the preceding compositions wherein the dentifrice base comprises an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS) by weight of the composition.
1.29. Any of the preceding compositions wherein the dentifrice base comprises a zwitterionic surfactant, for example a betaine surfactant, for example cocamidopropylbetaine, e.g. in an amount of from about 0.1% to about 4.5% by weight, e.g. 0.5-2% cocamidopropylbetaine by weight of the composition
1.30. Any of the preceding compositions wherein the dentifrice base comprises a viscosity modifying amount of one or more of polysaccharide gums, for example xanthan gum or carrageenan, silica thickener, and combinations thereof.
1.31. Any of the preceding compositions wherein the dentifrice base comprises gum strips or fragments.
1.32. Any of the preceding compositions wherein the dentifrice base comprises flavoring, fragrance and/or coloring.
1.33. Any of the foregoing compositions wherein the dentifrice base comprises an effective amount of one or more antibacterial agents in addition to the zinc-amino acid complex, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.
1.34. Any of the foregoing compositions wherein the dentifrice base comprises an antibacterially effective amount of triclosan, e.g. 0.1-0.5%, e.g. about 0.3% by weight of the composition.
1.35. Any of the preceding compositions wherein the dentifrice base comprises a whitening agent, e.g., a selected from the group consisting of peroxides, metal chlorites, perborates, percarbonates, peroxyacids, hypochlorites, and combinations thereof.
1.36. Any of the preceding compositions wherein the dentifrice base comprises hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);
1.37. Any of the preceding compositions wherein the dentifrice base comprises an agent that interferes with or prevents bacterial attachment, e.g., solbrol or chitosan.
1.38. Any of the preceding compositions wherein the dentifrice base comprises a soluble calcium salt, e.g., selected from calcium sulfate, calcium chloride, calcium nitrate, calcium acetate, calcium lactate, and combinations thereof.
1.39. Any of the preceding compositions wherein the dentifrice base comprises a physiologically or orally acceptable potassium salt, e.g., potassium nitrate or potassium chloride, in an amount effective to reduce dentinal sensitivity.
1.40. Any of the foregoing compositions wherein the dentifrice base comprises an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.

1.41. Any of the preceding compositions wherein the dentifrice base comprises a breath freshener, fragrance or flavoring.

1.42. Any of the foregoing compositions, wherein the pH of the composition is approximately neutral, e.g., about pH 7.

1.43. Any of the foregoing compositions wherein
the zinc-amino acid complex is ZLC in an amount of 2-6% by weight of the composition; and
the one or more soluble phosphate salts are selected from tetrasodium pyrophosphate (TSPP), sodium tripolyphosphate (STPP), tetrapotassium pyrophosphate (TKPP), and combinations thereof in an amount of 2-6% by weight of the composition; and
the dentifrice base comprises
an effective amount of a fluoride ion source,
silicas,
humectant,
thickener,
anionic surfactant, e.g., sodium lauryl sulfate,
zwitterionic surfactant, e.g., cocamidopropyl betaine
flavoring and sweetener.

1.44. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

The disclosure further provides methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of a composition of the disclosure, e.g., any of Composition 1, et seq. to the teeth, and optionally then rinsing with water or aqueous solution sufficient to trigger precipitation of zinc oxide from the composition.

The disclosure further provides a method of making a dentifrice comprising a zinc amino acid complex and one or more soluble phosphate salts, e.g., any of Composition 1, et seq. comprising combining a zinc ion source with an amino acid, in free or salt form (e.g., combining zinc oxide with lysine hydrochloride), in an aqueous medium, optionally isolating the complex thus formed in solid salt form, and combining the complex with the soluble phosphate salts in a dentifrice base.

For example, in various embodiments, the disclosure provides methods to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of Compositions 1, et seq. as described above to the oral cavity of a person in need thereof, e.g., one or more times per day. The disclosure further provides Compositions 1, et seq. for use in any of these methods.

The disclosure further provides the use of soluble phosphate salts, zinc and an amino acid to make an oral care composition comprising phosphate salts and a zinc-amino acid complex.

The disclosure further provides the use of a zinc amino acid complex, for example a zinc amino acid halide, for example a zinc-lysine-chloride complex, together with phosphate salts to reduce and inhibit acid erosion of the enamel, clean the teeth, reduce bacterially-generated biofilm and plaque, reduce gingivitis, inhibit tooth decay and formation of cavities, and/or reduce dentinal hypersensitivity.

Without intending to be bound by theory, it is believed that the formation of the zinc amino acid halide proceeds via formation of the zinc halide then coordination of amino acid residues around a central zinc. Using reaction of ZnO with lysine hydrochloride in water as an example, the zinc can react with lysine and/or lysine.HCl to form a clear solution of Zn-lysine-chloride complex ($ZnLys_3Cl_2$), wherein $Zn^{++}$ is located in an octahedral center coordinated with two oxygen and two nitrogen atoms in the equatorial plane coming from two lysine's carboxylic acids and amine groups respectively. The zinc is also coordinated to the third lysine via its nitrogen and carboxylic oxygen, at the apical position of the metal geometry.

In another embodiment, a zinc cation is complexes with two amino acid residues and two chloride residues. For example, where the amino acid is lysine, the complex has the formula $[Zn(C_6H_{14}N_2O_2)_2Cl]^+Cl^-$. In this complex, Zn cation is coordinated by two lysine ligands with two N atoms from $NH_2$ groups and O atoms from carboxylic groups in an equatorial plane. It displays a distorted square-pyramidal geometry with the apical position occupied by a $Cl^-$ atom. This novel structure gives rise to a positive cation moiety, to which a $Cl^-$ anion is combined to form an ionic salt.

Other complexes of zinc and amino acid are possible, and the precise form is dependent in part on the molar ratios of the precursor compounds, e.g., if there is limited halide, halide-free complexes may form, e.g. $ZnOLys_2$, having a pyramid geometry, with the equatorial plane that is same as the above compound (Zn is bound to two oxygen and two nitrogen atoms from different lysines), wherein the top of the pyramid is occupied by an O atom.

Mixtures of complexes and/or additional complex structures, e.g., involving multiple zinc ions based on the zinc structure, are possible and contemplated within the scope of the disclosure. When the complexes are in solid form, they may form crystals, e.g. in hydrated form.

Irrespective of the precise structure of the complex or complexes, however, the interaction of the zinc and the amino acid converts insoluble zinc oxide or zinc salts to a highly soluble complex at approximately neutral pH. With increasing dilution in water, however, the complex disassociates, and the zinc ion converts to insoluble zinc oxide. This dynamic is unexpected—typically ionic compositions become more soluble at higher dilution, not less—and this facilitates deposition of the zinc precipitate on the teeth upon administration, in the presence of saliva and with rinsing. This precipitation occludes the dentinal tubules, thereby reducing hypersensitivity, and also provides zinc to the enamel, which reduces acid erosion, biofilm and plaque formation.

It will be understood that other amino acids can be used in place of lysine in the foregoing scheme. It will also be understood that, although the zinc, amino acid and optionally halide may be primarily in the form of precursor materials or in the form of an ionic complex, there may be some degree of equilibrium, so that the proportion of material which is actually in complex compared to the proportion in precursor form may vary depending on the precise conditions of formulation, concentration of materials, pH, presence or absence of water, presence or absence of other charged molecules, and so forth.

In a particular embodiment, the active is provided in a toothpaste. Upon brushing, the active is diluted by saliva and water, leading to precipitation and the formation of deposits and occluding particles.

The benefits of the oral care compositions of the disclosure are numerous. By providing zinc ions and zinc containing compounds that can release zinc ions in oral cavities, the oral care compositions of the disclosure provide antimicrobial, antiplaque, antigingivitis, anti-malodor, anticaries, and anticalculus benefits. The occluding particles and the surface deposits are compounds containing zinc (particularly ZnO), as well as other zinc derivatives which can release zinc ions into oral cavities and provide the various benefits as recognized above. Additional benefits include but are not limited to anti-attachment, anti-periodontitis and anti-bone loss, as well as promotion of wound healing.

A second benefit is the antierosive properties of zinc ions, which form antierosive deposits on tooth surfaces through oxidation and hydrolysis. The surface deposits, as well as the occluding particles, can react with and neutralize acids, thus protecting the dental surface from the erosive effects of the acids. In this regard, the more surface depositions/occlusion the treatments lead to, the more efficacious the treatments are, and therefore zinc-arginine and zinc-lysine are preferred. It is also noted that when the surface deposits and occluding particles neutralize acids, beneficial zinc ions and amino acids (infra) can be released, providing oral care benefits other than anti-erosion.

A third benefit is anti-sensitivity benefit as a result of the occlusion. Occlusion of dentin tubules leads to sensitivity relief.

A fourth benefit is the benefit associated with amino acids. The occluding particles and surface deposits contain the corresponding amino acids, such as arginine and lysine. These amino acids provide multiple benefits. For example, basic amino acids lead to higher pH of the plaque and can provide anticaries benefits. In addition, it is also expected that arginine can enhance the activity of arginolytic bacteria, leading to a more healthy plaque. Arginine is also known to promote wound healing and collagen integrity.

Active Agents:

The compositions of the disclosure may comprise various agents which are active to protect and enhance the strength and integrity of the enamel and tooth structure and/or to reduce bacteria and associated tooth decay and/or gum disease, including or in addition to the zinc-amino acid complexes. Effective concentration of the active ingredients used herein will depend on the particular agent and the delivery system used. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly. For example, a triclosan toothpaste may contain about 0.3 wt % triclosan.

Fluoride Ion Source:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the disclosure may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the disclosure at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counterion in the salt.

Abrasives:

The compositions of the disclosure, e.g. Composition 1 et seq. include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Abrasives comprising insoluble or poorly soluble phosphate salts are not considered to fall within the "one or more soluble phosphate salts" referred to herein.

Other silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason. In certain embodiments, abrasive materials useful in the practice of the oral care compositions in accordance with the disclosure include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the disclosure are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present disclosure.

Foaming Agents:

The oral care compositions of the disclosure also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present disclosure. Polyoxyethylene is also commonly known as polyethylene glycol ("PEG") or polyethylene oxide. The polyoxyethylenes suitable for this disclosure will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present disclosure. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

Surfactants:

The compositions useful in the disclosure may contain anionic surfactants, for example:
i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
ii. higher alkyl sulfates, such as sodium lauryl sulfate,
iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$.
iv. higher alkyl aryl sulfonates such as sodium dodecyl benzene sulfonate (sodium lauryl benzene sulfonate)
v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the disclosure may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the disclosure, e.g., Composition 1, et seq., comprises sodium lauryl sulfate.

The surfactant or mixtures of compatible surfactants can be present in the compositions of the present disclosure in about 0.1% to about 5.0%, in another embodiment about 0.3% to about 3.0% and in another embodiment about 0.5% to about 2.0% by weight of the total composition.

Tartar Control Agents:

In various embodiments of the present disclosure, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The disclosure thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In one embodiment, tetrasodium pyrophosphate (TSPP), sodium tripolyphosphate (STPP), tetrapotassium pyrophosphate (TKPP), or mixtures thereof are used. In another embodiment, the compositions comprise a mixture of tetrasodium pyrophosphate (TSPP) and sodium tripolyphosphate (STPP)($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents: The oral care compositions of the disclosure may also include a flavoring agent. Flavoring agents which are used in the practice of the present disclosure include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight e.g. about 0.5 to about 1.5% by weight.

Polymers:

The oral care compositions of the disclosure may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The compositions of the disclosure may include an anionic polymer, for example in an amount of from about 0.05 to about 5%. Such agents are known generally for use in dentifrice, although not for this particular application, useful in the present disclosure are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

Water: The oral compositions comprise water. Water employed in the preparation of commercial oral compositions should be deionized and free of organic impurities. The amount of water in the compositions includes the free water which is added plus that amount which is introduced with other materials. The oral composition may comprise water in the amount of 1-20% by weight, e.g. 5-18% by weight, e.g. 7-19% by weight, e.g. 8-17% by weight, e.g., 9-16% by weight, about 10% by weight, and all ranges and sub ranges therebetween.

Humectants: Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerine, sorbitol, xylitol, propylene glycol as well as other polyols and mixtures of these humectants. In one embodiment of the disclosure, the principal humectant is glycerin, which may be present at levels of greater than 25%, e.g. 25-35% about 30%, with 5% or less of other humectants.

Other Optional Ingredients:

In addition to the above-described components, the embodiments of this disclosure can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Unless stated otherwise, all percentages of composition components given in this specification are by weight based on a total composition or formulation weight of 100%.

Unless otherwise specifically identified, the ingredients for use in the compositions and formulations of the present disclosure are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this disclosure, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the disclosure extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1—Low Water Dentifrice with ZLC

Formulation and Stability of Low Water Formulations

Dentifrice formulas containing ZLC are generated in a low water system with reproducible antibacterial efficacy. ZLC as a spray dried powder mixture of acidified zinc oxide and lysine (1%-6%, 0.14-0.80% zinc) is dissolved into the aqueous phase prior to addition to the gel system. In the test formulations, the amount of glycerin is adjusted accordingly based on the ZLC level. Surfactant and phosphate levels are consistent. ZLC can be dissolved with sodium fluoride and sodium saccharin or in a separate aqueous phase of at least 5% (w/w) water for complete dissolution. A matching placebo is generated with the absence of ZLC compensated by additional glycerin. One concern is stability of the ZLC in formulation with the fluoride, which possibly could interact deleteriously with the Zn complex. The initial physical evaluation as well as the stability measurements 4 weeks 40° C. for zinc and fluoride indicate minimal degradation of zinc and fluoride, e.g., formation of insoluble $ZnF_2$.

ZLC (6%) Low Water Dentifrice Formula

| Ingredients | Weight % |
| --- | --- |
| Demineralized Water | 10.00 |
| Sodium Saccharin | 0.80 |
| Sodium Fluoride | 0.24 |
| Tetrasodium Pyrophosphate | 2.00 |
| Sodium Tripolyphosphate | 3.00 |
| Glycerin (99.0-101.0%) | 43.84 |
| ZLC (Spray Dried Powder) | 6.00 |
| Polyethylene Glycol 600 | 3.00 |
| Propylene Glycol | 4.00 |
| Microcrystalline Cellulose/Sodium CMC NF | 1.00 |
| Sodium Hydroxide (50%) | 0.45 |
| Polyvinyl Pyrrolidone | 1.50 |
| Xanthan Gum | 0.25 |
| Carboxymethylcelullose Sodium | 0.30 |
| Syn, Amorph PPT Slica Abrasive | 12.00 |
| High Cleaning Silica | 12.00 |
| Sodium Lauryl Sulfate Powder | 1.75 |
| Cocamidopropyl Betaine | 1.00 |
| Flavor | 1.20 |
| Total Components | 100.00 |
| Total Zinc % | 0.80 |

ZLC (6%) Low Water Dentifrice Formula with STPP Only, 15% Water

| Ingredients | Weight % |
| --- | --- |
| Demineralized Water | 15.00 |
| Sodium Saccharin | 0.80 |
| Sodium Fluoride | 0.24 |
| Tetrasodium Pyrophosphate | 0.00 |
| Sodium Tripolyphosphate | 3.00 |
| Glycerin (99.0-101.0%) | 36.51 |
| ZLC (Spray Dried Powder) | 6.00 |
| Polyethylene Glycol 600 | 3.00 |
| Propylene Glycol | 4.00 |
| Microcrystalline Cellulose/Sodium CMC NF | 1.000 |
| Sodium Hydroxide (50%) | 0.450 |
| Polyvinyl Pyrrolidone | 1.500 |
| Xanthan Gum | 0.250 |
| Carboxymethylcelullose Sodium | 0.30 |
| Syn, Amorph PPT Slica Abrasive | 12.00 |
| High Cleaning Silica | 12.00 |
| Sodium Lauryl Sulfate Powder | 1.75 |
| Cocamidopropyl Betaine | 1.00 |
| Flavor | 1.20 |
| Total Components | 100.00 |
| Total Zinc % | 0.80 |

Placebo Low Water Dentifrice Formula

| Ingredients | Weight % |
| --- | --- |
| Demineralized Water | 10.00 |
| Sodium Saccharin | 0.80 |
| Sodium Fluoride | 0.24 |
| Tetrasodium Pyrophosphate | 2.00 |
| Sodium Tripolyphosphate | 3.00 |
| Glycerin (99.0-101.0%) | 42.94 |
| ZLC (Spray Dried Powder) | 0.00 |
| Polyethylene Glycol 600 | 3.00 |
| Propylene Glycol | 4.00 |
| Microcrystalline Cellulose/Sodium CMC NF | 1.00 |
| Sodium Hydroxide (50%) | 0.45 |
| Polyvinyl Pyrrolidone | 1.50 |

| Ingredients | Weight % |
|---|---|
| Xanthan Gum | 0.25 |
| Carboxymethylcelullose Sodium | 0.30 |
| Syn, Amorph PPT Silica Abrasive | 12.00 |
| High Cleaning Silica | 12.00 |
| Sodium Lauryl Sulfate Powder | 1.75 |
| Cocamidopropyl Betaine | 1.00 |
| Flavor | 1.20 |
| Total Components | 100.00 |
| Total Zinc % | 0.00 |

Fluoride and zinc dentifrice prototypes with ZLC plus sodium fluoride or sodium monofluorophosphate (MFP) are measured after four weeks storage at room temperature and at elevated temperature (40° C.).

|  | Prototype #1 (NaF) | Prototype #2 (MFP) |
|---|---|---|
| Initial Fluoride (ppm) | 1130 | 1120 |
| Room temperature 4 weeks Fluoride (ppm) | 1020 | 1050 |
| Accelerated 40° C. Fluoride 4 weeks (ppm) | 910 | 1000 |
| Initial Total Zinc (%) | 0.88 | 0.86 |
| Initial Soluble Zinc (%) | 0.58 | 0.61 |
| Accelerated 40° C. Zinc 4 weeks (%) | 0.85 | 0.95 |

Antimicrobial Efficacy of Low Water Formulations

Existing microbiological methods are generally not effective at detecting bacterial growth inhibition resulting from bacteriostatic actives, such as zinc compounds. Therefore, we have used modified methods to understand the efficacy of these formulas.

In order to understand the immediate effects of ZLC on mixed species, planktonic oral bacteria, we use the metabolic indicator dye resazurin. A five species mix of representative oral species is used in this assay (*Actinomyces viscosus, Lactobacillus casei, Streptococcus oralis, Fusobacterium nucleatum,* and *Veillonella parvula*) and treated with either 1:100 or 1:250 dilutions of dentifrice. Such low concentrations are needed in order to separate the effects of the zinc compounds from the surfactant effects of the formula, which are very strong on planktonic, laboratory strains of bacteria. Bacteria are incubated with dentifrice for 1 h prior to staining with 50 μg/ml of resazurin solution. When viable bacteria are incubated with resazurin, the blue, non-fluorescent dye is reduced by the bacteria to the pink fluorescent dye resorufin. Fluorescence of test samples is read at 560 nm excitation/590 nm emission and compared to the fluorescence of standardized mixes of live and dead bacteria to determine the percentage of the initial population that remained viable following treatment.

Previous work on ZLC found that when the resazurin assay is conducted in media, there is no reduction of efficacy upon dilution of the active ingredient, a dose response typically seen for Zn compounds. However, when these experiments are repeated in cell-free human saliva, a typical dose response occurred. Therefore, studies of ZLC dentifrices are conducted in filter-sterilized pooled human saliva, rather than an artificial medium or buffer. The results of this resazurin assay appear below.

| Formulation | % viable bacteria |
|---|---|
| Placebo formulation without ZLC 1:100 dilution | 89.75 |
| Placebo formulation without ZLC 1:250 dilution | 100.85 |
| 6% ZLC formulation, conventional base 1:100 dilution | 7.38 |
| 6% ZLC formulation, conventional base 1:250 dilution | 50.05 |
| 6% ZLC formulation, low water base 1:100 dilution | 6.36 |
| 6% ZLC formulation, low water base 1:250 dilution | 9.60 |

As can be seen in the table above, when 6% ZLC is formulated in a conventional dentifrice base containing ~30% water, the ZLC lends the formula considerable efficacy beyond that seen from the base. When the formula is further diluted (from 1:100 to 1:250), the expected dose response is seen. Whereas the 1:100 dilution left only 7.38% of the original population viable, the 1:250 left 50.05% viable. However, when the same 6% ZLC is formulated into a low water base containing only 10% water, the efficacy upon dilution to 1:250 remains almost as active as at 1:100. This suggests that, using the low water formula, ZLC remains active, even upon dilution.

Bioavailable assay of zinc in CP-4 containing dentifrices: 10-20% water, showing an optimal area of performance at 10-15%.

| % water | Percentage viability |
|---|---|
| 10% | 30.00 |
| 12% | 33.89 |
| 15% | 31.02 |
| 20% | 21.15 |

A low water dentifrice formulation with ZLC thus maintains the efficacy of the zinc active in antibacterial models, in some cases without the dose response observed upon testing in saliva. The formulation is compatible with fluoride ion sources, providing simultaneous anticaries effect.

Example 2—Effect of Phosphate on ZLC Formulations

The above examples describe the synthesis and efficacy of a zinc(bislysine) complex known as ZLC and its efficacy in a low water dentifrice formulation. It is well known from both our own work and literature that zinc interacts readily with phosphate compounds. The interaction is strong ($k_a$~$10^9$) preventing chelation by weaker organic molecules. Additionally, we have found in other experiments that the addition of phosphate salts to zinc complexes in neat solutions can decrease the amount of bioactive zinc that is readily available to interact with bacteria.

Based upon this previous work, we considered that the removal of the phosphate salt system from the low water dentifrice described in the above example should leave us with more free, bioavailable ZLC and would, therefore, improve the antimicrobial efficacy of the dentifrice formula. In order to test this hypothesis, we formulated the two dentifrices described as follows ZLC (6%) Low Water Dentifrice Formula with Full Phosphate System

| Ingredients | Weight % |
|---|---|
| Demineralized Water | 10.00 |
| Sodium Saccharin | 0.80 |
| Sodium Fluoride | 0.24 |
| Tetrasodium Pyrophosphate | 2.00 |
| Sodium Tripolyphosphate | 3.00 |
| Glycerin (99.0-101.0%) | 39.51 |
| ZLC (Spray Dried Powder) | 6.00 |
| Polyethylene Glycol 600 | 3.00 |
| Propylene Glycol | 4.00 |
| Microcrystalline Cellulose/Sodium CMC NF | 1.00 |
| Sodium Hydroxide (50%) | 0.45 |
| Polyvinyl Pyrrolidone | 1.50 |
| Xanthan Gum | 0.25 |
| Carboxymethylcelullose Sodium | 0.30 |
| Syn, Amorph PPT Slica Abrasive | 12.00 |
| High Cleaning Silica | 12.00 |
| Sodium Lauryl Sulfate Powder | 1.75 |
| Cocamidopropyl Betaine | 1.00 |
| Flavor | 1.20 |
| Total Components | 100.00 |
| Total Zinc % | 0.80 |

ZLC (6%) Low Water Dentifrice Formula without Phosphate Salts

| Ingredients | Weight % |
|---|---|
| Demineralized Water | 10.00 |
| Sodium Saccharin | 0.80 |
| Sodium Fluoride | 0.24 |
| Tetrasodium Pyrophosphate | 0.00 |
| Sodium Tripolyphosphate | 0.00 |
| Glycerin (99.0-101.0%) | 44.51 |
| ZLC (Spray Dried Powder) | 6.00 |
| Polyethylene Glycol 600 | 3.00 |
| Propylene Glycol | 4.00 |
| Microcrystalline Cellulose/Sodium CMC NF | 1.00 |
| Sodium Hydroxide (50%) | 0.45 |
| Polyvinyl Pyrrolidone | 1.50 |
| Xanthan Gum | 0.25 |
| Carboxymethylcelullose Sodium | 0.30 |
| Syn, Amorph PPT Slica Abrasive | 12.00 |
| High Cleaning Silica | 12.00 |
| Sodium Lauryl Sulfate Powder | 1.75 |
| Cocamidopropyl Betaine | 1.00 |
| VMC Plus Flavor K91-6764 | 1.20 |
| Total Components | 100.00 |
| Total Zinc % | 0.80 |

Phosphates Improve the Antibacterial Efficacy of ZLC in Dentifrice Formulations

As an initial evaluation of the ability of these formulas to interact with oral bacteria, they are tested in a resazurin-based viability assay described in the previous example, at a 1:250 dilution of dentifrice. This study is conducted in filter sterilized human saliva.

In this assay, the formula with no phosphates in it actually performed slightly better. This is not unexpected. It is well known that zinc compounds interact strongly with phosphate groups. Since this assay only measures the amount of freely bioavailable zinc present in the system over a relatively short period of time, it is likely that there is more free zinc available in the no phosphate system and able to interact with the bacteria. However, this assay would not demonstrate any negative impacts of increased free lysine (should the original chelate breakdown) or the long term benefits of a more stable ZLC complex.

| Formulation tested (250:1 dilution) | % viability of bacteria |
|---|---|
| Placebo formulation without ZLC | 25.46 |
| 6% ZLC, no phosphates | 8.77 |
| 6% ZLC, with phosphates | 14.73 |

Bacteria in the oral cavity are not generally found as free floating, single planktonic organisms. More often, they live in complex, structured, mixed species communities known as biofilms (plaque). In order to understand the efficacy of these two formulae, we tested the effect of repeated exposures to these dentifrices on model oral biofilms. In this assay, hydroxyapatite (HAP) discs are pre-treated for 2 min in a 1:1 slurry of toothpaste in water. Following rinsing in sterile media, discs are inoculated with 10% whole human saliva in SHI medium (insert reference). Discs are remove once every 24 h and treated for an additional 2 min, rinsed and returned to fresh SHI medium. This treatment is repeated for a total of 5 treatments. On the $5^{th}$ day, discs are harvested by incubating in 0.25% trypsin solution for 2 h. Total biomass is measured by reading the optical absorbance of each sample at 610 nm. Results are reported as a percent reduction relative to discs treated with sterile medium.

Surprisingly, in this assay the formula containing 6% ZLC and no phosphates actually appeared to promote growth of the biofilm, whereas the 6% ZLC formula containing TSPP and STPP reduced biofilm growth relative to a negative control. The original phosphate containing paste gave a 36.75% reduction in total biomass, as measured by optical density at 610 nm. Conversely, the phosphate-free paste gave less than a 1% reduction in total biomass. Additionally, in some trials of this experiment, it appeared that the biofilm growth was actually promoted by the treatment. Without intending to be bound by theory, it is believed that the growth promotion could be due to free lysine resulting from the breakdown of ZLC in the absence of phosphates.

| Biofilm inhibition | |
|---|---|
| | % reduction in biomass relative to media alone |
| 6% ZLC formulation with phosphates | 36.75 |
| 6% ZLC formulation without phosphates | 0.75 |

We pre-treated HAP discs with a simple solution of lysine to see how an overabundance of free lysine would affect biofilm formation. After 48 h, these biofilms visually were overgrown and looked very similar to the biofilms grown following repeated exposure to the 6% ZLC dentifrice without phosphates, further suggesting that phosphates are actually stabilizing the ZLC structure in its active form in a low water dentifrice, and that the ZLC itself can be taken up by the bacteria, providing antibacterial activity without prior release of lysine from the complex.

Phosphates Improve ZLC Formulation Aesthetics

It appears that phosphate salts in ZLC dentifrice formulations promote stability of the interaction between the zinc and lysine. Within the typical dentifrice formulation, the interaction between zinc and lysine can be perturbed by sodium lauryl sulfate (SLS) often used in toothpaste formulation to provide foam. The strength of coordination to zinc by phosphates and sulfates are similar. Should the zinc chelate sulfate, instead of lysine in a formula, the charge of the sulfate group would be neutralized. When this occurs, foam is lost in the formulation. To test this hypothesis a SITA foam analysis is performed on a ZLC formula with phosphates (low water ZLC with phosphates, as described above), a ZLC formula without phosphates (commercial formulation without phosphates, with ZLC added), and placebo without phosphates formula (commercial formulation without phosphates, without ZLC). All three formulations include sodium lauryl sulfate as foaming agent. The level of foam in the ZLC formulation with phosphates is comparable to the placebo formula—both show good foaming in the test. But in the ZLC formulation without phosphates, foam level is severely reduced, suggesting the breakdown of the zinc-lysine interaction, so that the zinc is available to interact with the SLS.

Example 3: Varying Ratios of ZLC and Different Phosphates

Example 2 describes the efficacy and aesthetics of a low water dentifrice formulation containing 6% ZLC. In order to further probe the contribution of ZLC to the antiplaque efficacy of this formulation, we prepared formulations containing 1%, 2% and 4% ZLC to examine the dose-dependent effects of this compound in oral care formulations. The level of glycerin is adjusted to compensate for the differential mass loss in formulations using the different levels of ZLC. LC (6%) Low Water Dentifrice Formula with Full Phosphate System

| Ingredients | Weight % |
| --- | --- |
| Demineralized Water | 10.00 |
| Sodium Saccharin | 0.80 |
| Sodium Fluoride | 0.24 |
| Tetrasodium Pyrophosphate | 2.00 |
| Sodium Tripolyphosphate | 3.00 |
| Glycerin (99.0-101.0%) | 39.51 |
| ZLC (Spray Dried Powder) | 6.00 |
| Polyethylene Glycol 600 | 3.00 |
| Propylene Glycol | 4.00 |
| Microcrystalline Cellulose/Sodium CMC NF | 1.00 |
| Sodium Hydroxide (50%) | 0.45 |
| Polyvinyl Pyrrolidone | 1.50 |
| Xanthan Gum | 0.25 |
| Carboxymethylcelullose Sodium | 0.30 |
| Syn, Amorph PPT Slica Abrasive | 12.00 |
| High Cleaning Silica | 12.00 |
| Sodium Lauryl Sulfate Powder | 1.75 |
| Cocamidopropyl Betaine | 1.00 |
| Flavor | 1.20 |
| Total Components | 100.00 |
| Total Zinc % | 0.8 |

ZLC (4%) Low Water Dentifrice Formula with Full Phosphate System

| Ingredients | Weight % |
| --- | --- |
| Demineralized Water | 10.00 |
| Sodium Saccharin | 0.80 |
| Sodium Fluoride | 0.24 |
| Tetrasodium Pyrophosphate | 2.00 |
| Sodium Tripolyphosphate | 3.00 |
| Glycerin (99.0-101.0%) | 41.51 |
| ZLC (Spray Dried Powder) | 4.00 |
| Polyethylene Glycol 600 | 3.00 |
| Propylene Glycol | 4.00 |
| Microcrystalline Cellulose/Sodium CMC NF | 1.00 |
| Sodium Hydroxide (50%) | 0.45 |
| Polyvinyl Pyrrolidone | 1.50 |
| Xanthan Gum | 0.25 |
| Carboxymethylcelullose Sodium | 0.30 |
| Syn, Amorph PPT Slica Abrasive | 12.00 |
| High Cleaning Silica | 12.00 |
| Sodium Lauryl Sulfate Powder | 1.75 |
| Cocamidopropyl Betaine | 1.00 |
| Flavor | 1.20 |
| Total Components | 100.00 |
| Total Zinc % | 0.53 |

ZLC (2%) Low Water Dentifrice Formula with Full Phosphate System

| Ingredients | Weight % |
| --- | --- |
| Demineralized Water | 10.00 |
| Sodium Saccharin | 0.80 |
| Sodium Fluoride | 0.24 |
| Tetrasodium Pyrophosphate | 2.00 |
| Sodium Tripolyphosphate | 3.00 |
| Glycerin (99.0-101.0%) | 43.51 |
| ZLC (Spray Dried Powder) | 2.00 |
| Polyethylene Glycol 600 | 3.00 |
| Propylene Glycol | 4.00 |
| Microcrystalline Cellulose/Sodium CMC NF | 1.00 |
| Sodium Hydroxide (50%) | 0.45 |
| Polyvinyl Pyrrolidone | 1.50 |
| Xanthan Gum | 0.25 |
| Carboxymethylcelullose Sodium | 0.30 |
| Syn, Amorph PPT Slica Abrasive | 12.00 |
| High Cleaning Silica | 12.00 |
| Sodium Lauryl Sulfate Powder | 1.75 |
| Cocamidopropyl Betaine | 1.00 |
| Flavor | 1.20 |
| Total Components | 100.00 |
| Total Zinc % | 0.27 |

ZLC (1%) Low Water Dentifrice Formula with Full Phosphate System

| Ingredients | Weight % |
| --- | --- |
| Demineralized Water | 10.00 |
| Sodium Saccharin | 0.80 |
| Sodium Fluoride | 0.24 |
| Tetrasodium Pyrophosphate | 2.00 |
| Sodium Tripolyphosphate | 3.00 |
| Glycerin (99.0-101.0%) | 44.51 |
| ZLC (Spray Dried Powder) | 1.00 |
| Polyethylene Glycol 600 | 3.00 |
| Propylene Glycol | 4.00 |
| Microcrystalline Cellulose/Sodium CMC NF | 1.00 |
| Sodium Hydroxide (50%) | 0.45 |
| Polyvinyl Pyrrolidone | 1.50 |
| Xanthan Gum | 0.25 |
| Carboxymethylcelullose Sodium | 0.30 |
| Syn, Amorph PPT Slica Abrasive | 12.00 |
| High Cleaning Silica | 12.00 |
| Sodium Lauryl Sulfate Powder | 1.75 |
| Cocamidopropyl Betaine | 1.00 |
| Flavor | 1.20 |
| Total Components | 100.00 |
| Total Zinc % | 0.13 |

In order to probe the impacts of ZLC levels on the potential antiplaque efficacy of these formulas, the above formulations are tested in a bacterial viability assay based on the metabolic indicator dye resazine, as described in the examples above, at a 1:250 dilution. In this assay, lower viability is indicative of more bioavailable zinc. The strong impact of other dentifrice ingredients in this assay is exemplified by the 25% viability observed in samples treated with the placebo formula. Increasing bioactivity can be seen with increasing ZLC levels, up to 4%. A plateau in efficacy is reached at 2% ZLC.

| Formulation at 1:250 dilution | % viable |
|---|---|
| 0% ZLC (control formulation) | 25.46 |
| 1% ZLC | 20.44 |
| 2% ZLC | 15.58 |
| 4% ZLC | 14.58 |
| 6% ZLC | 14.73 |

We also looked at the effects of these dentifrices in a mixed species, repeated exposure biofilm model. In this assay, hydroxyapatite (HAP) discs are pre-treated for 2 min in a 1:1 slurry of toothpaste in water. Following rinsing in sterile media, discs are inoculated with 10% whole human saliva in SHI medium (Tian, Y., et. al. Using DGGE profiling to develop a novel culture medium suitable for oral microbial communities. *Molecular Oral Microbiology.* 2010. 25 (5): 357-367). After 4 h incubation, discs are removed, treated for an additional 2 min, rinsed and returned to fresh, sterile SHI medium. Treatment is repeated once every 24 h for a total of 6 treatments (including the pretreatment). Following the final treatment, discs are allowed to recover for ~2 h and then incubated in 0.25% trypsin solution for 2 h, in order to dislodge the adherent biofilm. Total biomass is measured by reading the optical absorbance of each sample at 610 nm. Results are reported as a percent reduction relative to discs treated with sterile medium.

Aerobic biofilm measurements show the percent reduction in biofilm as a function of ZLC level; phosphates concentrations remain constant.

| Formulation | % reduction in biofilm relative to media |
|---|---|
| 0% ZLC (control formulation) | 60.39 |
| 1% ZLC | 59.83 |
| 2% ZLC | 84.95 |
| 4% ZLC | 70.36 |
| 6% ZLC | 63.25 |

In this assay, there appears to be a peak of activity from the 2% ZLC formulation. Further testing is carried out using the 2% ZLC formula, which demonstrates improved efficacy over the other concentrations and the 6% ZLC formula, which is the highest level of total active tested.

We hypothesized that some the improved efficacy of the 2% ZLC formula, contrary to the expected dose response, was driven by the interaction of ZLC with the phosphate salts present in the formula. Therefore, we investigated the efficacy of 6% ZLC dentifrices containing either no phosphate salts or one of the two salts in isolation from the other.

ZLC (6%) Low Water Dentifrice Formula with STPP Only

| Ingredients | Weight % |
|---|---|
| Demineralized Water | 10.00 |
| Sodium Saccharin | 0.80 |
| Sodium Fluoride | 0.24 |
| Tetrasodium Pyrophosphate | 0.00 |
| Sodium Tripolyphosphate | 3.00 |
| Glycerin (99.0-101.0%) | 41.51 |
| ZLC (Spray Dried Powder) | 6.00 |
| Polyethylene Glycol 600 | 3.00 |
| Propylene Glycol | 4.00 |
| Microcrystalline Cellulose/Sodium CMC NF | 1.00 |
| Sodium Hydroxide (50%) | 0.45 |
| Polyvinyl Pyrrolidone | 1.50 |
| Xanthan Gum | 0.25 |
| Carboxymethylcelullose Sodium | 0.30 |
| Syn, Amorph PPT Slica Abrasive | 12.00 |
| High Cleaning Silica | 12.00 |
| Sodium Lauryl Sulfate Powder | 1.75 |
| Cocamidopropyl Betaine | 1.00 |
| Flavor | 1.20 |
| Total Components | 100.00 |
| Total Zinc % | 0.80 |

ZLC (6%) Low Water Dentifrice Formula with TSPP Only

| Ingredients | Weight % |
|---|---|
| Demineralized Water | 10.00 |
| Sodium Saccharin | 0.80 |
| Sodium Fluoride | 0.24 |
| Tetrasodium Pyrophosphate | 2.00 |
| Sodium Tripolyphosphate | 0.00 |
| Glycerin (99.0-101.0%) | 42.51 |
| ZLC (Spray Dried Powder) | 6.00 |
| Polyethylene Glycol 600 | 3.00 |
| Propylene Glycol | 4.00 |
| Microcrystalline Cellulose/Sodium CMC NF | 1.00 |
| Sodium Hydroxide (50%) | 0.45 |
| Polyvinyl Pyrrolidone | 1.50 |
| Xanthan Gum | 0.25 |
| Carboxymethylcelullose Sodium | 0.30 |
| Syn, Amorph PPT Slica Abrasive | 12.00 |
| High Cleaning Silica | 12.00 |
| Sodium Lauryl Sulfate Powder | 1.75 |
| Cocamidopropyl Betaine | 1.00 |
| VMC Plus Flavor K91-6764 | 1.20 |
| Total Components | 100.00 |
| Total Zinc % | 0.80 |

These formula are first tested in the resazurin assay described above to understand the relative bioavailability of zinc in each formula. Dentifrices are tested at a 1:250 dilution; lower viability of bacteria is indicative of more bioavailable zinc.

| Formulation | % viable |
|---|---|
| 0% ZLC (placebo formulation) | 25.46 |
| 2% ZLC with phosphates | 15.58 |
| 6% ZLC with phosphates | 14.73 |
| 6% ZLC without phosphates | 8.77 |
| 6% ZLC TSPP only | 7.67 |
| 6% ZLC STPP only | 11.43 |

The results for this assay show (as was seen previously) the 2% ZLC and 6% ZLC formulas demonstrate similar in vitro activity with both more active than the placebo formula. Formulas containing either no phosphate salts or only TSPP demonstrated greater activity, suggesting that the zinc in these formulas is more readily available. Since this assay only measures the amount of bioavailable zinc present in the system over a relatively short period of time, it is likely that there is more zinc freely available in the no- or low-phosphate system and able to interact with the bacteria. However, this assay would not demonstrate any impacts of increased free lysine (due to breakdown of ZLC) or the potential long term benefits of a more stable ZLC complex.

In order to probe the longer term and repeated exposure impacts of these phosphate changes, the performance of these formulas is assessed in the biofilm assay described above.

Aerobic biofilm measurements show the percent reduction in biofilm as a function of ZLC level and presence or absence of specific phosphate salts.

| Formulation | % reduction vs media |
| --- | --- |
| 0% ZLC (placebo formulation) | 14.40 |
| 2% ZLC with phosphates (STPP/TSPP) | 32.53 |
| 6% ZLC, no phosphates | 0.74 |
| 6% ZLC with phosphates (STPP/TSPP) | 36.75 |
| 6% ZLC, TSPP only | 35.12 |
| 6% ZLC STPP only | 42.08 |

In this assay, the 2% ZLC formula gave a greater biofilm reduction than the majority of the formulas tested. A 6% ZLC formula with all of the phosphate salts removed gave very little measurable reduction in biofilm formation and, in fact, appeared to promote biofilm growth in some cases. Conversely, the dual phosphate system demonstrated biofilm inhibition similar to that observed with the 2% ZLC system. Although the formula with only TSPP showed similar performance to the dual phosphate system, the dentifrice formula containing only STPP actually had increased biofilm inhibition beyond that of the dual phosphate system.

Taken together, the data presented here suggest that the phosphates are able to complex with the ZLC in the dentifrice solution and form a unique compound with potential novel antiplaque benefits.

While the disclosure has been described with respect to specific examples including presently preferred modes of carrying out the disclosure, those skilled in the art will appreciate that there are numerous variations and permutations of the above described systems and techniques. It is to be understood that other embodiments may be utilized and structural and functional modifications may be made without departing from the scope of the present disclosure. Thus, the scope of the disclosure should be construed broadly as set forth in the appended claims.

We claim:

1. A dentifrice comprising
   a. a zinc-amino acid complex which is a zinc lysine chloride complex having the chemical structure [Zn(C$_6$H$_{14}$N$_2$O$_2$)$_2$Cl]$^+$Cl$^-$ ("ZLC"), either in solution of the cationic complex ([Zn(C$_6$H$_{14}$N$_2$O$_2$)$_2$Cl]$^+$) and the chloride anion, or in solid salt form;
   b. one or more soluble phosphate salts; and
   c. a dentifrice base,
   wherein the dentifrice comprises water in the amount of about 10% by weight of the composition.

2. The dentifrice of claim 1, wherein the zinc lysine chloride complex is in mono- or dihydrate form.

3. The dentifrice of claim 2 wherein the zinc-amino acid complex is present in an amount of 2-6% of the dentifrice by weight.

4. The composition of claim 1 wherein by "soluble phosphate salts" is meant orally acceptable phosphate salts having a solubility in water at 25° C. of at least 1 g/100 ml.

5. The composition of claim 1 wherein the one or more soluble phosphate salts are sodium and/or potassium salts of pyrophosphates and/or polyphosphates.

6. The composition of claim 1 wherein the one or more soluble phosphate salts comprise tetrasodium pyrophosphate (TSPP), sodium tripolyphosphate (STPP), tetrapotassium pyrophosphate (TKPP), or combinations thereof.

7. The composition of claim 1 wherein the one or more soluble phosphate salts are present in an amount of 2-8%, by weight of the composition.

8. The dentifrice of claim 1, wherein the dentifrice base comprises an effective amount of a fluoride ion source.

9. The dentifrice of claim 1, wherein the dentifrice base comprises ingredients selected from one or more of abrasives, buffering agents, humectants, surfactants, thickeners, gum strips or fragments, breath fresheners, flavoring, fragrance, coloring, antibacterial agents, whitening agents, agents that interfere with or prevents bacterial attachment, calcium sources, orally acceptable potassium salts, and anionic polymers.

10. The dentifrice of claim 1, wherein the dentifrice base comprises sodium lauryl sulfate.

11. The dentifrice of claim 1 wherein
   the zinc-amino acid complex is ZLC in an amount of 2-6% by weight of the composition; and
   the one or more soluble phosphate salts are selected from tetrasodium pyrophosphate (TSPP), sodium tripolyphosphate (STPP), tetrapotassium pyrophosphate (TKPP), and combinations thereof in an amount of 2-6% by weight of the composition; and
   the dentifrice base comprises
      an effective amount of a fluoride ion source,
      silicas,
      humectant,
      thickener,
      sodium lauryl sulfate,
      cocamidopropyl betaine
      flavoring and sweetener.

12. The dentifrice of claim 1, for use to reduce and inhibit acid erosion of the enamel, clean the teeth, reduce bacterially-generated biofilm and plaque, reduce gingivitis, inhibit tooth decay and formation of cavities, and/or reduce dentinal hypersensitivity.

13. A method of treating or reducing dental enamel erosion, cleaning the teeth, reducing bacterially-generated biofilm and plaque, reducing gingivitis, inhibiting tooth decay and formation of cavities, and/or reducing dentinal hypersensitivity comprising applying a dentifrice according to claim 1 to the teeth.

* * * * *

UNITED STATES PATENT AND TRADEMARK OFFICE
CERTIFICATE OF CORRECTION

PATENT NO. : 10,561,590 B2  
APPLICATION NO. : 16/142738  
DATED : February 18, 2020  
INVENTOR(S) : Gregory Szewczyk et al.

Page 1 of 1

It is certified that error appears in the above-identified patent and that said Letters Patent is hereby corrected as shown below:

On the Title Page

Item (54), Line 1, "COMPROMISING" should be replaced with –COMPRISING–.

Item (56), "OTHER PUBLICATIONS", Line 1, delete "O.T.Quimby" and insert --O.T. Quimby--.

In the Specification

In Column 1, Line 1, "COMPROMISING" should be replaced with –COMPRISING–.

In Column 3, Line 47, "e.g," should be replaced with –e.g.–.

In Column 4, Line 33, "1:3" should be replaced with –1:3.–.

In Column 4, Line 37, "thereof" should be replaced with –thereof.–.

In Column 5, Line 55, "composition" should be replaced with –composition.–.

In Column 6, Line 43, "persulfate);" should be replaced with –persulfate).–.

In Column 21, Line 26, "LC" should be replaced with –ZLC–.

Signed and Sealed this  
Ninth Day of June, 2020

Andrei Iancu  
*Director of the United States Patent and Trademark Office*